US012618094B2

(12) United States Patent
Wang et al.

(10) Patent No.: US 12,618,094 B2
(45) Date of Patent: May 5, 2026

(54) CORE-SHELL NANOPARTICLES, METHODS OF PRODUCING THE SAME, AND USES THEREOF FOR DETECTING EXTRACELLULAR POLYMERIC SUBSTANCES

(71) Applicant: CITY UNIVERSITY OF HONG KONG, Kowloon (HK)

(72) Inventors: Wen-Xiong Wang, Kowloon (HK); Neng Yan, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 594 days.

(21) Appl. No.: 18/091,357

(22) Filed: Dec. 29, 2022

(65) Prior Publication Data

US 2023/0212639 A1      Jul. 6, 2023

Related U.S. Application Data

(60) Provisional application No. 63/296,743, filed on Jan. 5, 2022.

(51) Int. Cl.
*C08L 25/12* (2006.01)
*C08L 25/14* (2006.01)
*C12Q 1/02* (2006.01)

(52) U.S. Cl.
CPC .............. *C12Q 1/02* (2013.01); *C08L 25/14* (2013.01); *C08L 2207/53* (2013.01)

(58) Field of Classification Search
CPC .......... C08L 25/14; C08L 25/06; C08L 33/08; C08L 33/10; C08K 5/01
USPC ........................................................ 523/201
See application file for complete search history.

(56) References Cited

U.S. PATENT DOCUMENTS

2006/0280798 A1* 12/2006 Ensoli ..................... A61P 37/04
                                                            424/188.1
2016/0211470 A1* 7/2016 Tang .................... C07D 407/06

* cited by examiner

*Primary Examiner* — Hannah J Pak
(74) *Attorney, Agent, or Firm* — Conley Rose, P.C.; Michael W. Piper; Gayatry S. Nair

(57) ABSTRACT

Disclosed herein is a core-shell nanoparticle exhibiting aggregation induced emission (AIE) properties. According to the embodiments of the present disclosure, the core-shell nanoparticle comprises a core and a shell layer encapsulating the core, in which the core comprises a polymeric matrix and one or more tetraphenylethane (TPE) embedded in the polymeric matrix. Preferably, the polymeric matrix is made of a hydrophobic polymer, and the shell layer is made of a hydrophilic polymer. Also disclosed herein are methods of producing the core-shell nanoparticle, and methods of detecting an extracellular polymeric substance (EPS) produced by a microorganism via using the core-shell nanoparticle.

6 Claims, 1 Drawing Sheet

10
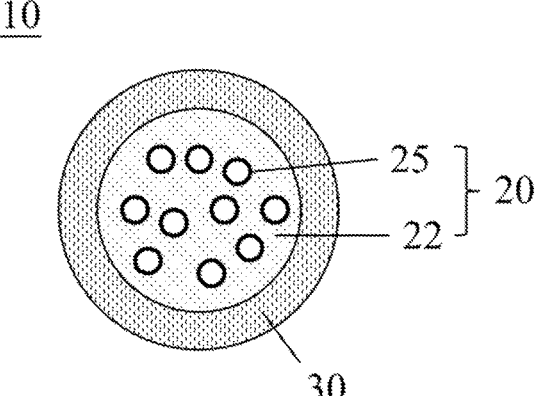

CORE-SHELL NANOPARTICLES, METHODS OF PRODUCING THE SAME, AND USES THEREOF FOR DETECTING EXTRACELLULAR POLYMERIC SUBSTANCES

CROSS-REFERENCE TO RELATED APPLICATIONS

This application relates to and claims the benefits of U.S. Provisional Application No. 63/296,743 filed Jan. 5, 2022; the content of which is incorporated herein by reference in its entirety.

BACKGROUND OF THE INVENTION

1. Field of the Invention

The present disclosure in general relates to the field of nanoparticles. More particularly, the present disclosure relates to a core-shell nanoparticle exhibiting aggregation induced emission (AIE) properties, and uses of the core-shell nanoparticle for detecting extracellular polymeric substance (EPS).

2. Description of Related Art

EPS is composed of complex high-molecular-weight mixtures of biopolymers exported from intracellular space by various microorganisms, such as microalgae, bacteria, and fungi, which subsequently form an extracellular polymeric matrix. The EPS matrix is considered as the "house of biofilm cells", attributable to the scaffold of the three-dimensional (3D) polymer networks accounting for more than 90% of biofilms. Functionally, EPS provides mechanical stability to the biofilms and protects the microorganisms from desiccation. It also acts as a barrier against adverse chemical and biological influences, such as osmotic stress, acid and/or base challenges, oxygen, antibiotics, antiseptics, host immune defense, and grazing protozoa. Moreover, it contributes to the sorption and storage of nutrients and trace elements as the location of numerous extracellular enzymatic reactions, and keeps the microorganisms in tight contact with each other to facilitate the genetic exchange and bacterial communication. As such, EPS production is considered as an important adaptation for microorganisms to their living environments.

Owing to their biocompatibility, non-toxicity, flexibility, biodegradability, and possibility to be recycled by biological processes, EPS is a promising platform for biotechnological, biomedical applications and therapeutic applications. Therefore, quantitative analysis the EPS produced by various microorganisms and monitoring the dynamic changes of EPS production are crucial to tailor their characteristics and optimize the amount of EPS produced. Numerous analytical techniques have been developed to characterize the components and spatial distribution of EPS, including Fourier transform infrared spectroscopy (FTIR), three-dimensional excitation-emission matrix fluorescence spectroscopy (3D-EEM), nuclear magnetic resonance spectroscopy (NMR), scanning electron microscopy (SEM), environmental scanning electron microscopy (ESEM), confocal laser scanning microscopy (CLSM), and atomic force microscopy (AFM). Among these methods, CLSM allows the in-situ and non-destructive visualization and quantification of the 3D structures of living and fully hydrated biofilms. A fluorescence labeling approach depends on the specificity of the selected stains, and multiple color staining technique and CLSM can together visualize the distribution of components of EPS in a biofilm. However, there is currently no fluorescence labeling method available for visualizing the EPS in general due to the highly complex and variable composition of the matrix produced by different microorganisms, their contrast spatial distribution patterns and highly dynamic properties. The conventional organic luminophores generally exhibit low resistance to photobleaching under strong laser irradiation, making these probes not suitable for long-term monitoring of EPS. In addition, they have small Stokes shift, resulting in strong self-absorption and low resolution, which makes them difficult for the real-time monitoring of the dynamic changes of EPS. Thus, development of novel fluorescent probes with improved properties for precise detection and long-term imaging is of great significance.

In view of the foregoing, there is a continuing interest in developing a novel fluorescent probe for detecting and long-term monitoring EPS.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a core-shell nanoparticle having AIE properties. According to some embodiments of the present disclosure, the core-shell nanoparticle in structure comprises a core and a shell layer encapsulating the core, in which the core comprises a polymeric matrix and one or more tetraphenylethane (TPE) embedded in the polymeric matrix.

According to some embodiments of the present disclosure, the polymeric matrix is made of a hydrophobic polymer. Preferably, the hydrophobic polymer is selected from the group consisting of polyethylene (PE), polystyrene (PS), polyvinylchloride (PVC), poly(N-vinylpyrrolidone) (PVP), polytetrafluorethylene (PTFE), polydimethylsiloxane (PDMS) and polyurethane (PUR). In one exemplary embodiment, the polymeric matrix is made of PS.

According to certain embodiments of the present disclosure, the shell layer is made of a hydrophilic polymer. Preferably, the shell layer is made of a copolymer consisting of two monomer units independently selected from the group consisting of methacrylic acid (MAA), methyl methacrylate (MMA), acrylic acid (AA), methyl acrylate, acrylamide, and ethylenimine. In one exemplary embodiment, the shell layer is made of a copolymer of MAA and AA.

According to some embodiments, the average diameter of the core-shell nanoparticle is about 140 nanometer (nm).

Also disclosed herein is a method of producing the core-shell nanoparticle of the present disclosure. The method comprises, (a) dissolving sodium dodecyl benzene sulfonate (SDBS) and ammonium bicarbonate in water;

(b) dispersing MMA, AA and styrene (St) in the solution of step (a) to produce a first mixture;

(c) adding a tetrahydrofuran (THF) solution of TPE into the first mixture of step (b) to produce a second mixture;

(d) adding ammonium peroxodisulfate (APS) into the second mixture of step (c) to produce a third mixture; and (e) stirring the third mixture of step (d) at 70-90° C. for at least 1 hour so as to produce the core-shell nanoparticle of the present disclosure.

According to some preferred embodiments, the TPE, MMA, AA and St are present in the second mixture at a mole ratio of 1:1-10:1-10:25-35. Preferably, the TPE, MMA, AA and St are present in the second mixture at a mole ratio of 1:1-5: 3-7:27-32. More preferably, the TPE, MMA, AA and St are present in the second mixture at a mole ratio of 1:2-4:4-6:28-30. In one specific example, the TPE, MMA, AA and St are present in the second mixture at a mole ratio of 1:3:5:29.

According to some exemplary embodiments, in the step (e), the third mixture is stirred at 80° C. for 10 hours.

Optionally, the method further comprises, (c-1) stirring the third mixture of step (c) at 70° C. for 0.5 hour prior to step (d).

According to certain embodiments, the core-shell nanoparticle of the present disclosure is useful in serving a bioprobe in staining and/or detecting EPS. Accordingly, another aspect of the present disclosure is directed a method of detecting EPS produced by a microorganism via using the present core-shell nanoparticle. The method comprises, (a) contacting the present core-shell nanoparticle with the microorganism;

(b) irradiating the product of step (a) with a light having an excitation wavelength of 405 nm; and (c) detecting the EPS via measuring the fluorescence emitted from the irradiated product of step (b) at a wavelength ranging from 450 to 550 nm.

Depending on desired purposes, the microorganism may be any of bacterium, yeast, fungus or microalgae.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1 is a schematic diagram depicting the core-shell nanoparticle 10 according to some embodiments of the present disclosure.

In accordance with common practice, the various described features/elements are not drawn to scale but instead are drawn to best illustrate specific features/elements relevant to the present invention.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here.

Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "aggregation induced emission" or "AIE" refers to the phenomenon manifested by compounds exhibiting significant enhancement of light-emission upon aggregation in the amorphous or crystalline (solid) states whereas they exhibit weak or almost no emission in dilute solutions. The term "AIEgen" refers to a molecule exhibiting ATE characteristics.

The term "nanoparticle" as used herein refers to a microscopic particle or particle population having a mean diameter less than 1,000 nanometers (nm); less than about 900 nm; less than about 800 nm; less than about 700 nm; less than about 600 nm; less than about 500 nm; less than about 400 nm; less than about 300 nm; less than about 200 nm; or less than 150 nm. Preferably, the term "nanoparticle" as used herein refers to a microscopic particle or particle population having a mean diameter ranging from 1 nm to less than 500 nm; from 10 nm to less than 400 nm; from 50 nm to less than 300 nm; from 100 nm to less than 200 nm; or from 130 to 150 nm. In an embodiment, more than 99% of the nanoparticles of a nanoparticle population have a mean diameter falling within a described range; more than about 90% of the microparticles have a mean diameter falling within a described range; more than about 80% of the microparticles have a mean diameter falling within a described range; more than about 70% of the microparticles have a mean diameter falling within a described range; more than about 60% of the microparticles have a mean diameter falling within a described range; more than about 50% of the microparticles have a mean diameter falling within a described range; more than about 40% of the microparticles have a mean diameter falling within a described range; more than about 30% of the microparticles have a mean diameter falling within a described range; more than about 20% of the microparticles have a mean diameter falling within a described range; or more than about 10% of the microparticles have a mean diameter falling within a described range. According to some preferred embodiments, the average diameter of the present nanoparticle is about 140 nm.

The term "core-shell nanoparticles" refers to a structural configuration of nanoparticles, in which an external layer formed of a second material encompasses an inner core of a first material, thereby forming the core-shell structure. The core-shell nanoparticle may have a regular shape (such as a nanosphere) or be irregularly shaped. Depending on desired purposes, the core-shell nanoparticle may have a cubic shape, needle shape, spherical shape, pyramidal shape, or polygonal cylindrical shape. According to some embodiments, the present core-shell nanoparticle has a spherical shape (i.e., a nanosphere).

The term "diameter" as used herein refers to the maximal length of a straight line segment passing through the center of a figure and terminating at the periphery. Although the term "diameter" is used normally to refer to the maximal length of a line segment passing through the center and connecting two points on the periphery of a nanosphere, it is also used herein to refer to the maximal length of a line segment passing through the center and connecting two points on the periphery of a nanoparticle having other shapes, such as a nanocube or an irregularly shaped nanoparticle.

As used herein, the term "polymer" refers to a large molecule (macromolecule) comprising of repeating structural units (i.e., monomer units) connected with covalent bonds usually thought to form a chain. The term "polymer" includes homopolymers (i.e., polymers resulting from the polymerization of a single monomer unit), copolymers (i.e., polymers formed by the polymerization reaction of at least two different monomer units), terpolymers (i.e., polymers formed by the polymerization reaction of at least three different monomer units), etc. The physical properties of a polymer are the result of the chemical nature of the structural units and their arrangement in space.

II. Description of the Invention

AIE is a photophysical phenomenon associated with chromophore aggregation. In the AIE process, non-emissive luminogens are induced to emit by the aggregate formation. Mechanistic studies indicated that restriction of intramolecular motion (RIM), which includes rotation and vibration, in the aggregated state is the main cause for the AIE effect. The luminogens exhibiting AIE attributes are termed "AIEgens". Various AIEgens have been designed and applied in various biological applications such as cell labelling and turn-on detection of biomacromolecules.

The present disclosure aims at providing a novel AIE-active nanoparticle, which enables specific staining of EPS produced by different microorganisms for the real-time tracing of EPS distribution changes in various living conditions. According to embodiments of the present disclosure, the AIE-active nanoparticle has a core-shell structure.

Reference is made to FIG. 1, which is a schematic diagram of the core-shell nanoparticle 10 according to some embodiments of the present disclosure. The core-shell nanoparticle 10 comprises, in its structure, a core 20, and a shell layer 30 encapsulating the core 20. The core 20 comprises a polymeric matrix 22 and an AIEgen 25 embedded in the polymeric matrix 22. According to the embodiments, the AIEgen is TPE.

According to some embodiments of the present disclosure, the polymeric matrix 22 is made of a hydrophobic polymer, and the shell layer 30 is made of a hydrophilic polymer. Non-limiting examples of the hydrophobic polymer suitable for producing the polymeric matrix 22 include, PE, PS, PVC, PVP, PTFE, PDMS, PUR, and a combination thereof. Exemplary hydrophilic polymers suitable for producing the shell layer 30 include, but are not limited to, MAA, MMA, AA, methyl acrylate, acrylamide, ethylenimine, and a combination thereof. According to one exemplary embodiment, the polymeric matrix 22 is made of PS, and the shell layer 30 is made of a copolymer of MAA and AA (i.e., P(MMA-AA)); the thus-produced core-shell nanoparticle 10 has a PS-P(MMA-AA) structure.

As could be appreciated, the average diameter of the core-shell nanoparticle 10 may vary with intended purpose. In general, the average diameter of the core-shell nanoparticle 10 is about 10 to 1,000 nm; for example, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1,000 nm. Preferably, the average diameter of the core-shell nanoparticle 10 is about 100 to 300 nm. More preferably, the average diameter of the core-shell nanoparticle 10 is about 130 to 150 nm. According to some specific examples, the core-shell nanoparticle having an average diameter of 140 nm is useful for staining EPS in a precise and efficient manner.

Also disclosed herein is a method of producing the present core-shell nanoparticle described above. The method comprises, (a) dissolving an emulsifying agent and a buffer agent in water;

(b) dispersing at least one hydrophobic monomer unit and at least one hydrophilic monomer unit in the solution of step (a) to produce a monomer mixture;

(c) adding AIEgen into the monomer mixture of step (b) to produce a monomer-AIEgen mixture;

(d) adding APS into the monomer-AIEgen mixture of step (c) to produce a monomer-AIEgen-APS mixture; and (e) stirring the monomer-AIEgen-APS mixture of step (d) at 70-90° C. for at least 1 hour so as to produce the core-shell nanoparticle of the present disclosure.

Specifically, in the step (a), the emulsifying and buffer agents are first dissolved in water. Depending on desired purpose, the emulsifying agent may be anionic, cationic or nonionic. Examples of emulsifying agent commonly used in the art for the polymerization reaction include, but are not limited to, sodium lauryl sulfate (SLS), sodium dodecyl sulfate (SDS), sodium cholate, sodium deoxycholate (DOC), sodium dodecyl benzene sulfonate (SDBS), dihexyl sodium sulfosuccinate, dioctyl sodium sulfosuccinate, lauryl ammonium chloride, lauryl ammonium bromide, stearyl ammonium chloride, stearyl ammonium bromide, lauryl dimethyl ammonium chloride, lauryl dimethyl ammonium bromide, stearyl dimethyl ammonium chloride, stearyl dimethyl ammonium bromide, lauryl trimethyl ammonium chloride, lauryl trimethyl ammonium bromide, stearyl trimethyl ammonium chloride, stearyl trimethyl ammonium bromide, lauryl amido betaine, potassium perfluorooctylacetate, and a combination thereof. Regarding the buffer agent, it may be any buffers known to regulate the pH value of the polymerization system; for example, ammonium biborate, ammonium carbonate, ammonium bicarbonate, ammonium pentaborate, ammonium tetraborate, ammonium hydroxide, or a combination thereof. According to certain embodiments, the emulsifying agent is SDBS, and the buffer agent is ammonium bicarbonate.

In the step (b), at least one hydrophobic monomer unit (i.e., the monomer unit for synthesizing a hydrophobic polymer during the polymerization reaction) and at least one hydrophilic monomer unit (i.e., the monomer unit for synthesizing a hydrophilic polymer during the polymerization reaction) are added to the solution of step (a) so as to produce a monomer mixture. Preferably, the hydrophobic monomer unit is selected from the group consisting of, ethylene, styrene, vinyl chloride, N-vinylpyrrolidone, tetrafluoroethylene, dimethylsiloxane, urethane, and a combination thereof; and the hydrophilic monomer unit is selected from the group consisting of MAA, MMA, AA, methyl acrylate, acrylamide, ethylenimine, and a combination thereof. According to some embodiments of the present disclosure, the monomer mixture contains styrene (as the hydrophobic monomer) for forming hydrophobic PS, and MAA and AA (as the hydrophilic monomers) for forming hydrophilic copolymer P(MMA-AA). Based on the hydrophilic and hydrophobic interactions, the thus-produced core-shell nanoparticle, from the inner core to the outer shell, has a PS-P(MMA-AA) structure.

Then, in the step (c), an AIEgen is added into the monomer mixture of step (b) (i.e., the mixture of emulsifying agent, buffer agent and monomer units) so as to produce a monomer-AIEgen mixture. According to the embodiments of the present disclosure, the AIEgen is TPE dissolved in THF. Preferably, the TPE, MMA, AA and styrene are present in the monomer-AIEgen mixture at a mole ratio of 1:1-10:1-10:25-35; in this case, the average diameter the thus-produced core-shell nanoparticle is about 140 nm, which, according to working examples of the present disclosure, is able to stain the EPS expressed on cell surface without internalizing into the cytoplasm of cells. According to some preferred embodiments, the TPE, MMA, AA and St are present in the monomer-AIEgen mixture at a mole ratio of 1:1-5:3-7:27-32. More preferably, the TPE, MMA, AA and St are present in the monomer-AIEgen mixture at a mole ratio of 1:2-4:4-6:28-30. In one specific example, the TPE, MMA, AA and St are present in the monomer-AIEgen mixture at a mole ratio of 1:3:5:29 (0.3:0.93:1.46:8.73).

Preferably, the monomer-AIEgen mixture of step (c) (i.e., the mixture of emulsifying agent, buffer agent, monomer units and AIEgen) is stirred at 70° C. for 0.5 hour.

Next, in the step (d), APS, an oxidizing agent commonly used as a polymerization initiator, is added to the monomer-AIEgen mixture of step (c) (i.e., the mixture of emulsifying agent, buffer agent, monomer units and AIEgen), so as to produce a monomer-AIEgen-APS mixture.

Finally, in the step (e), the polymerization is carried out by incubating the monomer-AIEgen-APS mixture of step (d) (i.e., the mixture of emulsifying agent, buffer agent, monomer units, AIEgen and APS) at 70-90° C. (e.g., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C. or 90° C.) for at least 1 hour (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5 or 12 hours, or longer) with continuous stirring. According to certain examples, the polymerization reaction is carried out at 80° C. for 10 hours.

According to certain examples of the present disclosure, the core-shell nanoparticle produced by the present method has a hydrophobic core (e.g., a PS core), and a hydrophilic shell layer (e.g., a P(MMA-AA) shell layer) encapsulating the hydrophobic core, in which the AIEgen (e.g., TPE) is embedded in the hydrophobic core. In some preferred examples, the hydrophilic shell layer is made of copolymer P(MMA-AA), in which the carboxyl group formed by the AA on the surface enhances the water dispersibility of the core-shell nanoparticle, and the surface negative charge allows the core-shell nanoparticle to be captured and retained in EPS.

Another aspect of the present disclosure provides a method of detecting the EPS produced by a microorganism by using the present core-shell nanoparticle. The method comprises, (a) contacting the present core-shell nanoparticle with the microorganism;

(b) irradiating the product of step (a) with a light having an excitation wavelength of 405 nm; and (c) detecting the EPS via measuring the fluorescence emitted from the irradiated product of step (b) at a wavelength ranging from 450 to 550 nm.

Depending on intended purpose, the microorganism may be a bacterium (e.g., *Synechococcus bacillaris*), yeast (e.g., *Saccharomyces cerevisiae*), fungus (e.g., *Aspergillus tereus*) or microalgae (e.g., *Chlamydomonas reinhardtii* or *Chlorella vulgaris*).

In the step (a), the microorganism is exposed to the present core-shell nanoparticle for a period of time (e.g., 30, 35, 40, 45, 50 or 55 minutes, or 1, 1.5, 2, 2.5, 3, 3.5, 4, 4.5 or 5 hours) so that the present core-shell nanoparticle is attached to the EPS. According to certain embodiments, the microorganism is exposed to at least 1 µM of the present core-shell nanoparticle, for example, 1, 2, 3, 4, 5, 6, 7, 8, 9, 10, 11, 12, 13, 14, 15, 16, 17, 18, 19 or 20 µM of the present core-shell nanoparticle. In one preferred embodiment, the exposure of the microorganism to 5 µM of the present core-shell nanoparticle for 30 minutes is sufficient to achieve the EPS-staining purpose.

Then, in the steps (b) and (c), the mixture of the microorganism and the present core-shell nanoparticle is irradiated with a light having an excitation wavelength of 405 nm thereby exciting the EPS-bound nanoparticle (step (b)), followed by measuring the fluorescence emitted from the irradiated product at a wavelength ranging from 450 to 550 nm (step (c)). As could be appreciated, the fluorescence may be detected by any techniques known in the art for detecting or quantifying fluorescent signals, for example, fluorescence microscopy (such as confocal fluorescence microscopy), flow cytometer, or a combination thereof.

According to certain embodiments, the core-shell nanoparticle and/or method of the present disclosure is useful in detecting and/or monitoring the 3D framework of microbial EPS.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Preparation of Monodispersed AIEgen-Containing Poly (Styrene-Methyl Methacrylate-Acrylic Acid) Nanoparticles The emulsifier sodium dodecyl benzene sulfonate (SDBS, 5 mg) and ammonium bicarbonate (0.15 g) were dissolved in 10 mL water, and MA/IA (0.93 mmol), AA (1.46 mmol) and St (8.73 mmol) mixture were dispersed in the solution. The AIEgen tetraphenylethane (TPE) in THF (5 wt % polymer, 2 mL) was dropwise added into the above solution. After stirring the reaction mixture at 70° C. for 0.5 h, the aqueous solution of ammonium peroxodisulfate (APS, 0.1 g in 2 mL water) was injected slowly. The polymerization was carried out at 80° C. for 10 h with continuous stirring. Driven by the hydrophilic and hydrophobic interaction, the nanoparticles formed the PS-P(MMA-AA) core-shell structure and the AIEgens were physically embedded in PS.

Characterization of the Synthesized Nanoprobe

The resulting monodispersed luminescent nanoparticles were centrifuged and washed with water three times. The size and morphology of the nanoparticles were characterized by scanning electron microscope (SEM). Photoluminescence (PL) spectra of the nanoparticles were recorded on a spectrofluorometer. Chemical composition of nanoprobe was characterized by Fourier-transform infrared spectroscopy (FTIR).

To investigate the photostability of the nanoprobe, 10 μM of nanoprobe was mixed with various concentrations of glycerol (0% to 90%, m/v) or glucosamine (0% to 99%, m/v), and the PL signal was monitored. The stability of nanoprobe in different medium (DI water, WC medium, F/2 medium and fileted artificial seawater) was also monitored by the addition of 10 μM nanoprobe. The hydrodynamic diameter and ζ potential of nanoprobe were determined by a Zeta potential analyzer equipped with a He—Ne laser ($\lambda$=633 nm, max 5 mW) and operated at a scattering angle of 173°. At different time points, the size distribution of nanoprobe was monitored, respectively. There were three replicates for each treatment.

Microorganisms

Marine cyanobacteria (*Synechococcus bacillaris*, CCMP 1333) were grown in f/2 media (a common and widely used general enriched seawater medium designed for growing coastal marine algae) under continuous illumination at a photon flux density of 50 μE/m$^2$/s at 24° C. on a 14/10 light/dark cycle. Cell growth was monitored by a traditional hemocytometer-based method under the microscope. Yeast (*Saccharomyces cerevisiae*, W303) was inoculated in yeast extract-peptone-dextrose (YPD) broth at around 185,000 cells/mL and cultured (30° C., 200 rpm) for 24 h. The obtained yeast was preserved at 4° C. until further use (within one week). Cell density was monitored by a microplate reader at Optical Density (OD) values (600 nm). Freshwater green alga *Chlamydomonas reinhardtii* (*C. reinhardtii*) was cultured in artificial WC (Woods Hole Chu-10) medium (containing 36.8 mg/L CaCl$_2$·2H$_2$O, 37 mg/L MgSO$_4$·7H$_2$O, 12.6 mg/L NaHCO$_3$, 11.4 mg/L K$_2$HPO$_4$·3H$_2$O, 85 mg/L NaNO$_3$, 21.1 mg/LNa$_2$SiO$_3$.9H$_2$O, micronutrients and vitamin solution) with bubbled air (26° C., 60 μE/m$^2$/s, on a 14/10 light/dark cycle). The cell density of the concentrated algae was measured using a hemocytometer under an optical microscope. The marine alga *Chlorella vulgaris* (*C. vulgaris*) was cultured in f/2 medium using filtered artificial seawater with bubbled air (26° C., 60

μE/m$^2$/s, on a 14/10 light/dark cycle). The cell density was measured by cell counts using a hemocytometer an optical microscope.

Staining EPS Produced by Microorganisms

Toxicity experiments for the yeast were conducted in DI water. Briefly, exponentially growing yeast cells in YPD medium were collected and washed twice in DI water and re-suspended in DI water to a cell density of OD$_{600\ nm}$ 1.2 (about 2×10$^7$ CFU/mL; CFU: colony forming unit). Then, 75 μL of the cell suspension was added into the wells of 96-well microplates containing 75 μL of various concentrations of nanoprobe in DI water. After 3-h incubation, yeast cells under different exposure conditions were analyzed by colony-forming units (CFU) and the toxic effects on the yeast could be obtained.

For the staining of microorganisms, 5 μM of nanoprobe was respectively added into the culture medium of different microorganisms (cyanobacteria, 1×10$^7$ cells/mL, F/2 medium; Yeast, 1×10$^7$ CFU/mL, DI water; *C. reinhardtii*, 1×10$^6$ cells/mL, WC medium; *C. vulgaris*, 1×10$^7$ cells/mL, f/2 medium). After 30 min, the microorganisms were collected, washed with DI water, then samples were placed in 1% glutaraldehyde for 10 min before being subjected to confocal imaging. For the nanoprobe (EPS imaging), excitation wavelength: 405 nm, emission wavelength: 450-550 nm. For the cyanobacterial autofluorescence, excitation wavelength: 488 nm, emission wavelength: 600-740 nm. For the yeast autofluorescence, excitation wavelength: 488 nm, emission wavelength: 495-520 nm. For *C. reinhardtii* autofluorescence, excitation wavelength: 405 nm, emission wavelength: 600-700 nm. For *C. vulgaris* autofluorescence, excitation wavelength: 405 nm, emission wavelength: 600700 nm. After imaging, the confocal data were analyzed using software for the signal distribution, 3D reconstruction and colocalization analysis.

Tracing the EPS Produced by *C. reinhardtii*

10$^6$ cells/mL of *C. reinhardtii* were exposed to different concentrations of nanoprobe (0 to 10 μM). After staining for 30 min, the algal cells were collected, washed and analyzed by flow cytometer using DAPI channel. A total of ≥20,000 events were acquired per sample. Data were analyzed using software. The stained samples were also examined by confocal microscope using nanoprobe and algal autofluorescence channels. After collecting the data, the line scan analysis could differentiate the EPS and algal autofluorescence, and the EPS thickness at the algal cell surface was obtained.

The EPS stained with nanoprobe was compared the commercial fluorescein isothiocyanate (FITC) probe stained EPS. A FITC solution (10 g/L, 10 μL) was added into the algal culture medium with a cell density of 1×10$^6$ cells/mL. After staining for 1 h at room temperature, the mixture was washed with DI water and resuspended into the culture medium and then stained with nanoprobe at a concentration of 5 μM. After further staining for 30 min, the algal cells were collected, washed, fixed with 1% glutaraldehyde for 10 min. The algae were then analyzed using confocal microscope using FITC channel (excitation wavelength: 488 nm, emission wavelength: 495-520 nm) and nanoprobe channel (excitation wavelength: 405 nm, emission wavelength: 450550 nm). The signal distribution and colocalization analysis were conducted by software.

To investigate the feasibility and potential applications of proposed nanoprobe for EPS staining, the algae at an initial concentration of 1×10$^5$ cells/mL were culture under different temperatures (20° C., 60 μE/m$^2$/s; 23° C., 60 μE/m$^2$/s; 26° C., 60 μE/m$^2$/s and 28° C., 60 μE/m$^2$/s), light intensities (26°

C., 30 µE/m$^2$/s; 26° C., 60 µE/m$^2$/s; 26° C., 120 µE/m$^2$/s and 26° C., 240 µE/m$^2$/s), nutrients (N-limit, 1/1000 of N added; P-limit, 1/1000 of P added; N-starvation, no N added; P-starvation, no P added), pH values (5.8, 6.5, 7.1, 7.6 and 8.1), and metals (Cu, Zn, Cd, Pb, Hg and Ag). After 48 h (or 72 h for metal experiments), the algal cell density was counted using the hemocytometer and photosynthetic capability was evaluated. Besides, the EPS thickness of algae under different conditions was also evaluated by exposing the algae to 5 µM of nanoprobe and stained for 30 min before analysis by confocal microscope.

Tracing the EPS Produced by Cyanobacteria

To investigate the feasibility and potential applications of proposed nanoprobe for EPS staining, the cyanobacteria at an initial concentration of 1×10$^7$ cells/mL were culture under different temperatures (20° C., 50 µE/m$^2$/s; 24° C., 50 µE/m$^2$/s and 28° C., 50 µE/m$^2$/s), light intensities (24° C., 25 µE/m$^2$/s; 24° C., 50 µE/m$^2$/s and 24° C., 100 µE/m$^2$/s), and pH values (5.6, 6.7, 7.5, 8.1 and 8.7). After 48 h, the cell density was counted using the hemocytometer and photosynthetic capability was evaluated. Besides, the EPS volume of cyanobacterial colony under different conditions was evaluated by exposing the cyanobacteria to 5 µM of nanoprobe and stained for 30 min before analysis by confocal microscope. After obtaining the confocal images, the data was analyzed by software for 3D reconstruction, cell counting in the 3D structure and EPS volume calculation.

Quantification of EPS Production

The EPS production of algae was also evaluated by extraction of EPS. Then the cells were separated by centrifugation at 12,000×g for 15 min at 4° C., and the cell-free supernatant was analyzed for EPS using glucose as standard.

Statistical Analysis

Statistical analyses were performed with software. Student's t test (t test) was used to compared two independent groups, such as the control group and one of the treatments, while the ANOVA extended the t-test to more than two groups. A p-value less than 0.05 (typically ≤0.05) was statistically significant.

Example 1 Characterization of the AIE-Active Nanoprobe

The ATE-active nanoprobe was synthesized by incorporating the AIEgens in the inner side and the polystyrene (PS) was coated on the surface, which was chemically stable. Poly(methyl methacrylate-acrylic acid) (i.e., P(MMA-AA)) copolymers were also added and formed coating agents at the PS surface. Further, the addition of acrylic acid monomer during the synthesis process resulted in the carboxyl groups on the AIE-NPs surface, which could enhance the water dispersibility of the AIE-active nanoprobe. After synthesis and purification, the size morphology of synthesized AIE-active nanoprobe was characterized by TEM. The nanoprobes were monodispersed and spherical with the averaged sized of 139.65±1.17 nm (data not shown). Under the excitation condition, the AIE-active nanoprobe emitted an intense greenish-blue light at 468 nm, and strong linear correlation between the concentration of nanoprobe (0 to 30 µM) and fluorescence intensity (y=9.410x−4.38, R$^2$=0.990) was found (data not shown). The detection limit of the nanoprobe by PL was 0.71 nM, suggesting that the nanoprobe was particularly bright at such low concentration.

EPS are complex biosynthetic polymers in terms of chemical composition, which are mainly composed of polysaccharides, structural proteins, enzymes, nucleic acids, lipids, and other compounds such as humic acids. To further investigate the stability of the AIE-active nanoprobe, AIE-active nanoprobe was independently added into different culture media, including DI water, WC medium, F/2 medium and seawater. The data indicated that the nanoprobe was stable in terms of size distribution and fluorescence intensity and within the 10% variation during the 600 min exposure (data not shown). Further, the nanoprobe was exposed into solutions with different concentrations of glycerol (monomers of lipids) and glucosamine (amino sugar, precursor for biochemical synthesis of glycosylated proteins and lipids, containing positively charged groups). The AIE-active nanoprobe emitted strong fluorescence and the fluorescence intensity was stable at different concentrations of the glycerol and glucosamine (data not shown), suggesting that the AIE-active nanoprobe could be highly fluorescent when mixed with hydrophobic moieties or water solubility components containing positively charged groups. Besides, the biocompatibility of the AIE-active nanoprobe towards different microorganisms was evaluated. No obvious toxic effect was observed (data not shown), suggesting that the AIE-active probe was biocompatible and showed great potential for the in situ noninvasive staining of the EPS produced by different microorganisms.

Example 2 Staining of EPS by the Synthesized Nanoprobe

Given the biocompatibility, strong stability (both the fluorescence properties and size distribution) of AIE-active nanoprobe and particularly bright under relatively low concentration, the AIE-active nanoprobe has a great potential to trace the EPS excreted by different microorganisms. Cyanobacteria, fungi, and some microalgal species are the major EPS producers, despite the composition of the matrix produced are different. These four microorganisms were chosen in the present study. It was found that the nanoprobe was absorbed at the surface of the microorganisms, exhibiting distinct distribution patterns as compared to the autofluorescence emitted from different types of microorganisms, with the Pearson's correlation coefficient of 0.175, 0.146, 0.04, and 0.03 for cyanobacteria, yeast, *Chlorella* and *C. reinhardtii*, respectively (data not shown). Contrasting to the cell surface EPS distribution in yeast, Chlorella or *C. reinhardtii*, the EPS excreted by the cyanobacteria was dispersed heterogeneously and covered the whole colony (data not shown). Therefore, the AIE-active nanoprobe could effectively stain the EPS produced by these four different microorganisms, despite the composition of the produced EPS varied. More importantly, the AIE-active nanoprobe exhibited great potential as the universal probe for staining the EPS produced by different microorganisms with great advantages over most of the commercialized probes.

Example 3 Optimization of the Staining of Microbial EPS Produced by *C. reinhardtii*

To verify the effectiveness of the proposed AIE-actively nanoprobe, the EPS imaging results using the proposed AIE nanoprobe were compared to that of the commercial EPS probe (fluorescein isothiocyanate, FITC), which was an amine reactive dye and stained all proteins and amino sugars of cells and EPS. The majority of FITC signals was distributed on the algal cell surface but around 15% of the FITC signals were detected in the cytoplasm, suggesting that the FITC could stain the EPS produced by algae (data not shown). FITC molecules are fluorescein fluorochrome conjugated to an isothiocyanate (ITC) that covalently binds to proteins and amine groups, which could directly bind to the cell membrane, resulting in small amount of molecules penetrating into the cell membranes ultimately. Compared with FITC staining, limited fluorescence signals derived from the AIE-active nanoprobe were detected in cytoplasm (less than 4%; data not shown). Further, strong colocalization was found between the FITC signals (the whole algal cells signals) and nanoprobe, with the Pearson's correlation coefficient of 0.703 (data not shown). However, the Pearson's correlation coefficient was more than 0.8 compared to the extracellular FITC signals (exclude intracellular signals) with nanoprobe signals (data not shown). Further, the photostability of the AIE-active nanoprobe was evaluated by continuously irradiating the nanoprobe stained algal samples under the confocal microscope imaging. After 1,500 s continuous irradiation, the fluorescence intensity of nanoprobe channel was relatively stable (10% difference during the measurement), while the fluorescence intensity of FITC channel decreased from 100% to around 40%, which implied that the AIE-active nanoprobe was much more stable than the commercial FITC (data not shown). Therefore, the AIE-active nanoprobe could specifically structuralize the EPS distribution at the algal cell surface. The proposed AIE-active nanoprobe was more advantageous over the commercial FITC probe in terms of specificity/precision and photostability, with potential for long-term tracing of the dynamic changes of EPS thickness under different living conditions.

The AIE-active nanoprobe was then utilized to quantitatively analyze the EPS distribution in *C. reinhardtii*. The exposure concentration of AIE-active nanoprobe was firstly optimized and its staining efficiency was investigated. The fluorescence intensity of nanoprobe signals detected in the algal cells increased with the increase of exposure concentration and saturated when the concentration of nanoprobe was around 5 µM (data not shown). The exposure concentration of AIE-active nanoprobe directly influenced the precision for mapping the EPS thickness (data not shown). At nanoprobe concentration <5 the obtained EPS thickness increased with increasing concentration probably due to the staining efficiency. However, once the exposure concentration of nanoprobe was higher than 5 µM (ranging from 5 µM to 10 µM), the detected EPS remained constant at around 3.66 µm (data not shown). Therefore, 5 µM could reach the highest fluorescence intensity for the staining of EPS and the staining efficiency of the nanoprobe could be more than 90%.

After optimizing the exposure concentration of the nanoprobe, the potential for the AIE-active nanoprobe for quantitative analysis of the EPS distribution was further explored. After staining with AIE-active nanoprobe, two distinct fluorescence signals were visualized for the algal samples. The red signal stands for the autofluorescence of algae that derived from the Chlorophyll while the blue signal stands for the EPS originated from the nanoprobe (data not shown). The EPS were coated on the induvial algal cell surface and exhibited distinct distribution patterns compared with the autofluorescence of algae (data not shown). Besides, the EPS thickness could be obtained by the line scanning of the EPS signals in the captured confocal images, which was about 3.58 µm (data not shown).

The EPS staining efficiency of AIE-active nanoprobes of different sizes (40 to 260 nm) was evaluated. The size of nanoprobe was controlled by changing the ratio between AIEgen and St/AA/MMA monomers. While smaller sized nanoprobe (43.5 nm, 70.8 nm and 84 nm) were internalized and distributed in the cytoplasm of algal cells, the relatively larger sized nanoprobe (140 nm, which was prepared by mixing the TPE, MMA, AA and St at a mole ratio of 0.3:0.93:1.46:8.73) were attached on the cell surface (data not shown). The 260 nm nanoprobe was only weakly attached on the algal surface, with distinct distribution patterns compared to the autofluorescence of the algae (data not shown). Therefore, the size of nanoprobe played a vital role for the EPS staining, and 140 nm nanoprobe was chosen due to their relatively higher staining precision and efficiency.

To further investigate the mechanisms of nanoprobe for tracing the EPS produced by microalgae, the nanoprobe was exposed to *C. reinhardtii*. After 30 min staining, *C. reinhardtii* were collected and the SEM imaging was used to study the staining mechanisms of the nanoprobe (data not shown). The control experiment was also conducted by analyzing *C. reinhardtii* (without nanoprobe exposure) using SEM imaging (data not shown). The nanoprobe was absorbed and retained in EPS on the algal cell surface while the size of nanoprobe remained unchanged compared with the original synthesized size (data not shown).

Collectively, the proposed AIE-active nanoprobe could effectively stain the EPS distribution in *C. reinhardtii*, showing great advantageous over the commercial probe in terms of staining specificity/precision, staining efficiency and the photostability. It could also be utilized to quantitatively analyze the EPS thickness at the algal surface. Potential EPS staining with the AIE-active nanoprobe was associated with the size, surface charge, and lipophilicity of the fluorophore. The AIE-active nanoprobe could be well dispersed in the exposure medium due to the negatively charged carboxyl groups. These AIE-active nanoprobe could easily absorb on algal cell surface and be retained in the EPS due to their slimy texture and ionic charges matrix, instead of being internalized into the algae. The lipophilic components in AIE nanoprobe could interact with hydrophobic moieties (fatty acids, alanine, leucine, glycine and deoxy sugars), which could enhance the retention of the AIE nanoprobe, resulting in the lighting up of the EPS. The proposed potential mechanisms for the staining of EPS by proposed ATE-active nanoprobe have great implications for designing highly efficient EPS probe by controlling their size, charge, and lipophilicity.

Example 4 Tracing the EPS Produced by *C. reinhardtii*

EPS plays an important role in the microalgae since its function as energy reservoir and defensive system against the unfavored conditions. Therefore, the EPS production should be closely related to their immediate living environment. The EPS in *C. reinhardtii* was coated at the algal cell surface and the EPS thickness varied at different layers (data not shown). To get an insight into the mechanisms of EPS distribution changes, it is necessary to quantitatively analyze the EPS distribution under different living environment. *C. reinhardtii* were thus cultured under different light intensities (30 µE/m²/s, 60 µE/m²/s, 120 µE/m²/s and 240 µE/m²/s), temperatures (20° C., 23° C., 26° C. and 28° C.), nutrient concentrations (N/P-limit, 1/1000 of cultured N/P concentration; N/P-starvation, no addition of N/P), pH values (5.8, 6.5, 7.1, 7.6 and 8.1), and the presence of different metals (Cu, Zn, Cd, Pb, Hg and Ag). Compared with algae under normal conditions (3.76±0.29 µm, 26° C.), a decrease of temperature significantly reduced the EPS thickness, which was 2.82±0.20 µm and 3.15±0.36 µm for the algae cultured under 20° C. and 23° C., respectively. Although the EPS thickness increased for algae under 28° C. (4.20±0.69 μm) compared to those under normal condition, no significant difference (p=0.08, Student's t-test) was found (data not shown). EPS thickness was significantly lower for algae under low light (30 μE/m²/s, 2.97±0.25 p<0.001), and thicker EPS was detected for algae under stronger light (120 μE/m²/s, 4.41±0.27 p<0.001; 240 μE/m²/s, 4.78±0.29 p<0.001), compared with the normal condition (3.76±0.29 μm, 60 μE/m²/s) (data not shown). Under N/P limited conditions, the EPS thickness was much lower (N-limited, 2.03±0.13 μm; P-limited, 2.15±0.18 μm) than that of algae under normal conditions. Much thinner EPS was detected for algae without N (1.24±0.17 μm) or P (1.14±0.17 μm) addition (data not shown). Therefore, the culture conditions of algae could significantly influence their EPS distribution. Furthermore, EPS thickness of algae measured by confocal imaging was compared with the EPS production quantified by EPS extraction and TOC measurement (data not shown). Similar tendency in the total EPS production with the EPS thickness was documented, suggesting that the AIE-active nanoprobe was reliable for the EPS staining and differentiated the EPS thickness changes under different living conditions. Since the pH of the culture medium was important for the algae, the thickness of EPS produced by algae under different pH conditions was further analyzed. EPS was relatively thinner at lower pH (2.59±0.09 μm at pH=5.8; 3.54±0.07 μm at pH=6.5) or higher pH (3.22±0.06 μm at pH=7.6; 2.49±0.09 μm at pH=8.1), as compared the produced EPS under normal pH condition (3.69±0.06 μm at pH=7.1) (data not shown).

EPS acted as a protective barrier of microbial cells when facing the stress. The correlation between stress tolerance of algae and their EPS thickness was further studied. The algae were exposed to different concentrations of metals (Cu, Zn, Cd, Pb, Hg and Ag) for 72 h, and the 50% effective concentrations (EC50) were calculated (data not shown). The EPS thickness was positively correlated with the 72-h EC50 of algae for all six metals, with correlation coefficient>0.8. Algae with much thicker EPS exhibited stronger tolerance with a much higher 72-h EC50. This is the first study to elucidate the correlation between the EPS thickness and the algal stress tolerance and resistance, and demonstrated that the EPS thickness played important role for stress tolerance of algae towards the metals.

Example 5 Tracing the 3D Framework of Cyanobacterial EPS

In contrast to *C. reinhardtii*, cyanobacteria are more likely to form macroscopic colonies to protect the cells from potential negative environmental impacts such as toxicants. Colony size of cyanobacteria was positively correlated with the content of EPS, which formed 3D framework surrounding the colonies. Under different conditions, the colony of cyanobacteria could vary in terms of size and morphology. The proposed AIE-active nanoprobe could specifically stain the EPS produced by cyanobacteria and exhibited distinct biodistribution patterns compared with that of cyanobacterial autofluorescence (data not shown). Besides, these excreted EPS were heterogeneously distributed in the cyanobacterial colony rather than coated on the individual cyanobacterial cell surface (data not shown), which was different from that of *C. reinhardtii*. The produced EPS formed complex 3D spatial structures covering the whole cyanobacterial colony, which varied at different depths (data not shown). The 3D volume of produced EPS in the cyanobacterial colony under optimal conditions (24° C., temperature; 50 μE/m²/s, light intensity) was 2.90±0.13 μm³/cell, and decreased to 1.39±0.12 μm³/cell at 20° C. and 1.279±0.05 μm³/cell at 28° C. (data not shown). EPS volume also decreased from 0.98±0.07 μm³/cell to 0.40±0.05 μm³/cell with increasing light intensity from 25 μE/m²/s to 100 μE/m²/s (data not shown). The optimal temperature and light conditions for cyanobacteria (*Synechococcus bacillaris*) were 24° C. and 50 μE/m²/s, respectively. Photoinactivation of the photosynthetic reaction center II occurred with changing temperature, and even a few degrees variation could induce the inhibitory effects on carbon fixation between internal and external metabolic pools. Besides, changes in light intensity induced the light stress on the cyanobacterium *Synechococcus bacillaris* and lowered the EPS production, consequently reducing the EPS volumes. EPS production was also affected by the pH condition, which was relatively lower when the cyanobacteria were cultured under either the lower (1.56±0.07 μm³/cell at pH=5.6; 2.73±0.15 μm³/cell at pH=6.7) or higher pH conditions (2.92±0.09 μm³/cell at pH=8.1; 0.98±0.08 μm³/cell at pH=8.7) (data not shown).

Correlation between the cyanobacterial photosynthesis and EPS volume was further investigated. Cyanobacteria cultured under different light intensities and temperatures were collected for confocal imaging (their EPS volume) and PAM analysis (photosynthesis capability, especially the maximum photosynthetic efficiency (Fv/Fm)) (data not shown). There was a strong correlation between the EPS volume of cyanobacteria and their maximum photosynthetic efficiency (correlation coefficient, >0.8; data not shown), suggesting that the EPS volume was strongly correlated with the cyanobacterial photosynthetic efficiency. Therefore, living conditions of cyanobacteria could be effectively influenced by EPS volume.

In conclusion, the present disclosure provides a novel AIE-active nanoprobe for the in-situ visualization of EPS distribution produced by different types of microorganisms, including the cyanobacteria, yeast, *C. reinhardtii* and marine species *C. vulgaris*. The present nanoprobe possesses greater advantageous over the commercial EPS probe in terms of staining efficiency, precision and photostability. The novel probe was used to monitor the EPS produced by *C. reinhardtii* and cyanobacteria due to their distinct distribution patterns. The EPS was coated on the algal cell surface and its thickness was significantly related to temperature, light intensity, nutrient conditions, pH, as well as algae stress tolerance. In contrast to phytoplankton, EPS produced by cyanobacteria formed complex 3D spatial structures covering the whole cyanobacterial colony. Their volume consistently decreased when the temperature or light intensity changed from the optimal conditions, probably attributable to the decrease in photosynthetic capability. These results collectively proved the feasibility of the nanoprobe for the staining of EPS distribution produced by different types of microorganisms and quantitative analysis of the EPS distribution under different living conditions.

It will be understood that the above description of embodiments is given by way of example only and that various modifications may be made by those with ordinary skill in the art. The above specification provides a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A core-shell nanoparticle having aggregation induced emission (AIE) properties, comprising, a core comprising a polymeric matrix and one or more tetraphenylethane (TPE) embedded in the polymeric matrix, wherein the polymeric matrix is made of a hydrophobic polymer; and a shell layer encapsulating the core, wherein the shell layer is made of a hydrophilic polymer.

2. The core-shell nanoparticle of claim 1, wherein the hydrophobic polymer is selected from the group consisting of polyethylene (PE), polystyrene (PS), polyvinylchloride (PVC), poly (N-vinylpyrrolidone) (PVP), polytetrafluorethylene (PTFE), polydimethylsiloxane (PDMS) and polyurethane (PUR).

3. The core-shell nanoparticle of claim 2, wherein the hydrophobic polymer is PS.

4. The core-shell nanoparticle of claim 1, wherein the hydrophilic polymer is a copolymer consisting of two monomer units independently selected from the group consisting of methacrylic acid (MAA), methyl methacrylate (MMA), acrylic acid (AA), methyl acrylate, acrylamide, and ethylenimine.

5. The core-shell nanoparticle of claim 4, wherein the copolymer consists of two monomer units of MAA and AA.

6. The core-shell nanoparticle of claim 1, wherein the average diameter of the core-shell nanoparticle is about 140 nm.

\* \* \* \* \*